(12) United States Patent
Franklin et al.

(10) Patent No.: US 6,327,491 B1
(45) Date of Patent: Dec. 4, 2001

(54) CUSTOMIZED SURGICAL FIXTURE

(75) Inventors: Ronald J. Franklin, Bowdoinham; Joel I. Franck, Durham; Frederick C. Haer, Brunswick, all of ME (US)

(73) Assignee: Neutar, LLC, Bowdoinham, ME (US)

( * ) Notice: Subject to any disclaimer, the term of this patent is extended or adjusted under 35 U.S.C. 154(b) by 0 days.

(21) Appl. No.: 09/110,070

(22) Filed: Jul. 6, 1998

(51) Int. Cl.$^7$ ........................................................ A61B 5/05
(52) U.S. Cl. ................................................................ 600/429
(58) Field of Search ............................... 600/429, 407, 600/417; 606/130; 378/205, 207, 62; 623/901; 164/45

(56) References Cited

U.S. PATENT DOCUMENTS

| | | | |
|---|---|---|---|
| 4,805,615 | * | 2/1989 | Carol ........................................ 606/130 |
| 5,116,345 | * | 5/1992 | Jewell et al. ............................ 606/130 |
| 5,222,499 | * | 6/1993 | Allen et al. ............................. 600/407 |
| 5,263,956 | * | 11/1993 | Nobles ...................................... 606/130 |
| 5,298,115 | | 3/1994 | Leonard . |
| 5,300,076 | * | 4/1994 | Leriche ..................................... 606/130 |
| 5,365,996 | * | 11/1994 | Crook ......................................... 164/45 |
| 5,370,692 | | 12/1994 | Fink et al. . |
| 5,397,329 | * | 3/1995 | Allen ........................................ 606/130 |
| 5,595,703 | | 1/1997 | Swaelens et al. . |
| 5,627,949 | | 5/1997 | Letcher, Jr. . |
| 5,638,819 | * | 6/1997 | Manwaring et al. ................. 600/407 |
| 5,702,406 | | 12/1997 | Vilsmeier et al. . |
| 5,728,106 | | 3/1998 | Misko et al. . |
| 5,732,703 | * | 3/1998 | Kalfas et al. .......................... 600/407 |
| 5,741,215 | | 4/1998 | D'Urso . |
| 5,768,134 | | 6/1998 | Swaelens et al. . |
| 5,776,143 | * | 7/1998 | Adams ..................................... 606/130 |
| 5,807,252 | * | 9/1998 | Hassfeld et al. ....................... 600/407 |
| 5,823,778 | | 10/1998 | Schmitt et al. . |
| 5,891,157 | * | 4/1999 | Day et al. ................................ 606/130 |
| 5,891,158 | * | 4/1999 | Manwaring et al. .................. 606/130 |
| 5,967,982 | * | 10/1999 | Barnett ..................................... 600/429 |
| 5,978,696 | * | 11/1999 | VomLehn et al. ...................... 600/411 |
| 5,980,535 | * | 11/1999 | Barnett et al. .......................... 606/130 |
| 5,987,349 | * | 11/1999 | Schulz ...................................... 600/427 |
| 6,006,126 | * | 12/1999 | Cosman ................................... 600/426 |
| 6,011,987 | * | 1/2000 | Barnett ..................................... 600/414 |
| 6,026,315 | * | 2/2000 | Lenz et al. .............................. 600/414 |

FOREIGN PATENT DOCUMENTS

WO 95/13758  5/1995  (WO) .
WO 96/11624  4/1996  (WO) .

* cited by examiner

Primary Examiner—Brian L. Casler
(74) Attorney, Agent, or Firm—Fish & Richardson P.C.

(57) ABSTRACT

A surgical fixture is formed by scanning a body to form a three-dimensional image of the body, and then identifying in the image a target point in the body, and mounting structures on the body. A model, such as a computer solid model, of the fixture is specified in accordance with the locations of the target point and mounting structures. The fixture is formed in accordance with the model of the fixture, for example using a rapid prototyping and tooling machine.

12 Claims, 12 Drawing Sheets

CUSTOMIZED SURGICAL FIXTURE

BACKGROUND

The invention relates to customized surgical fixtures.

Many types of surgical procedures rely on precisely guiding an instrument into the body. This is the case in stereotactic surgery in which a target point within a body, for example, within a brain, is identified in a three-dimensional scanned image of the body. A detailed survey of stereotactic surgery can be found in *Textbook of Stereotactic and Functional Neurosurgery*, P. L. Gildenberg and R. R. Tasker (eds.), McGraw-Hill, June 1997 (ISBN: 0070236046). In a typical approach to stereotactic surgery, a frame is attached to the body prior to scanning. After scanning, the target point in the body is identified in the scanned image with reference to the frame. Then, during surgery, an adjustable instrument guide is attached to the frame. The guide is adjusted to align with the target point. A related approach to stereotactic surgery is described in copending U.S. patent application Ser. No. 09/063,658 filed Apr. 21, 1998, which is incorporated herein by reference. In that approach applied to brain surgery, an adjustable instrument guide is attached directly to the skull. Once attached, it is adjusted to align with the target point.

These previous approaches to stereotactic surgery require adjustment of an instrument guide in order that the instrument can be driven accurately to the target point within the body.

SUMMARY

Adjusting an instrument guide to align with a target point within the body can be complex and time consuming. In some procedures multiple points must be targeted. For example, in spinal sterotactic surgery, multiple targets on different spinal segments are used. In a general aspect of the invention, rather than targeting an adjustable instrument guide, a customized fixture is fabricated for a particular patient, such that targeting is unnecessary or greatly simplified. A fixed instrument guide attached to the customized fixture can be used to guide a surgical instrument to the desired point without adjustment.

In one aspect, the invention features a method for forming a surgical fixture for attaching to a body and providing a reference structure for precisely locating a target within the body. The method includes processing a three-dimensional scanned image of the body, for example a CAT or MRI scan. The scanned image includes the target within the body, for example a point or region of the body, and a mounting location of the body. The method also includes determining a structure of the surgical fixture such that when attached at the mounting location of the body the fixture provides a reference structure in a determined location and orientation with respect to the target within the body.

The method can include one or more of the following features.

Multiple mounting points can be identified in the scanned image. The geometric relationship between corresponding mounting points on the fixture and the reference structure can then be determined. The method can further include attaching mounting anchors to the body prior to scanning the body. Scanning markers are attached to the anchors. The identified mounting points are then the locations of the scanning markers in the three-dimensional image.

The mounting location for the fixture can be an anatomical structure on the body. A contour of a surface of the fixture is determined to mate with the anatomical structure.

The method can include identifying the target in the scanned image. Also, a trajectory for reaching the target can be identified. The location and orientation of the reference structure is then determined with respect to the identified trajectory.

The structure of the fixture can be determined in terms of solid model of the fixture which defines the volume enclosed by the surface of the fixture. The method can then also include fabricating the fixture according to the solid model.

The method can include attaching the surgical fixture to the body and guiding an instrument to the target with reference to the attached surgical fixture.

The body can include a spine and the mounting location can include a spinal segment. The method can also include forming a model of the spine. The method can further include forming a corrected model of the spine in a corrected configuration. The determined structure of the surgical fixture is such that when attached, the fixture provides a second reference structure in a determined location and orientation with respect to the target in the corrected configuration of the spine.

The method can include selecting a model of a standard fixture and deforming the model of the standard fixture in to match the standard model to the target and the mounting location.

In another aspect, the invention features a surgical fixture formed from a computer model using a rapid prototyping and tooling technique. The fixture includes multiple mounting sections for attaching the fixture to a body at a predetermined mounting location on a body and a reference structure coupled to the mounting sections for guiding a surgical instrument into the body. When the fixture is attached to the body at the mounting location the reference structure is at a predetermined location and orientation to a target within the body. The fixture can include an instrument guide mounted on the reference structure for driving the instrument into the body.

In another aspect, the invention features software stored on a computer readable medium for causing a computer to perform the functions of processing a three-dimensional scanned image of a body, the scanned image including the target within the body and a mounting location of the body and determining a structure of a surgical fixture such that when attached at the mounting location of the body the fixture provides a reference structure in a determined location and orientation with respect to a target within the body.

Advantages of the invention include avoiding the need for targeting of an adjustable guidance fixture based on the location of target points within the body. This reduces the time required for surgery, and can increase the accuracy and precision of targeting.

Another advantage is that the customized fixture can provide a mounting base in a precise location relative to the body. This avoids a manual registration procedure of stereotactic surgery in which a correspondence between the scanned image and the physical body is established. The manual registration procedure can be time consuming and inaccurate.

Another advantage is that the customized fixture is easily attached to the body, for instance by mating the fixture to a set of anchors attached to the body prior to scanning, or in another instance, mating the fixture to the particular anatomy of the patient.

Another advantage of the invention is that the detailed fixture design can be based on a desired configuration of a configurable portion of the body, such as the spine, rather than solely on the configuration during scanning. This allows the fixture to be used not only to guide instruments into the body, but when attached to the body, to constrain the configuration of the body.

Other features and advantages of the invention will be apparent from the following description, and from the claims.

DESCRIPTION

An approach to stereotactic surgery according to the invention involves four phases.
1. Scanning and Surgical Planning. A three-dimensional scanned image of a patient is taken. A surgeon identifies a target point or volume within the body and determines coordinates of the target in the image.
2. Fixture Design. Based on the scanned image and the identified target point, a computer "solid model" of a customized fixture is computed. The solid model is computed so that the resulting fixture can be precisely attached to the body. The fixture is further designed to include an integral instrument guide, or a mounting base for a removable guide, for accurately positioning a surgical instrument at the target point when the fixture is attached to the body.
3. Fixture Fabrication. Based on the computed solid model, the customized fixture is fabricated using a computer controlled rapid prototyping and tooling (RPT) technique.
4. Surgery. The fabricated customized fixture is attached to the patient, and a surgical instrument is guided to the target point using the fixture.

Brain Surgery

A first embodiment of the invention is directed to brain surgery. Several alternative embodiments, described below, are also directed to brain surgery. Additional related embodiments are also applicable to other types of surgery, including spinal surgery. The first embodiment, which is directed to brain surgery, is described below following the four phases summarized above.

Scanning and Surgical Planning Phase

Figure 1A:
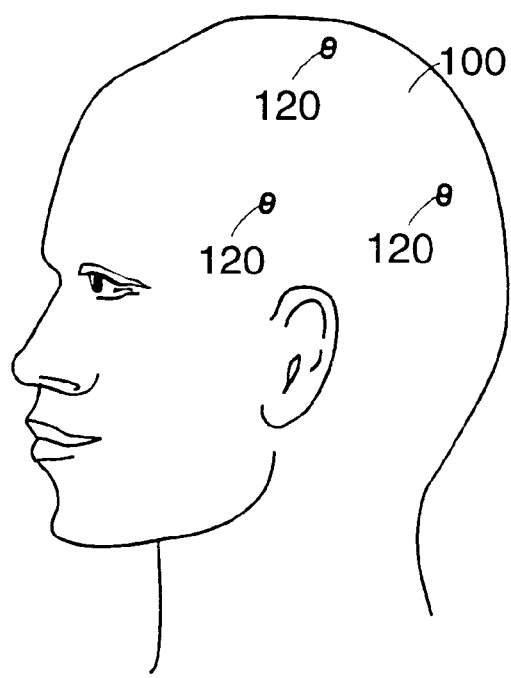
FIGS. 1a–b show scanning markers and bone anchors used to attached the scanning markers to a skull.

Referring to FIG. 1a, in the first phase, the scanning and surgical planning phase, a set of bone anchors 120 is attached to the skull 100 prior to scanning the patient. In the illustrative example shown in FIG. 1, three bone anchors 120 are attached to the skull. A greater or smaller number of anchors can also be used. During the later surgical phase, bone anchors 120 will be the attachment points for the fabricated fixture.

Figure 1B:
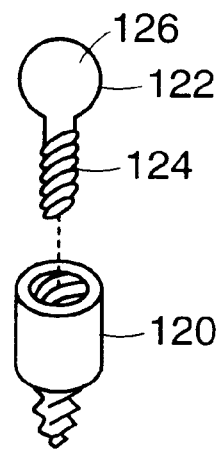

Referring to FIG. 1b, each of the bone anchors 120 has a threaded opening for accepting threaded bolts or other threaded attachments. In particular, prior to scanning, each threaded opening is used to accept a scanning marker 122. Each scanning marker 122 includes a threaded section 124 attached to a marker portion 126. Marker portion 126 includes a material that will result in a visible image in the scanned image. Various types of scanning techniques can be used, including CAT, PET, MRI, and SPECT. The material in the marker portions 126 is chosen depending on the scanning technique that will be used.

Figure 2:
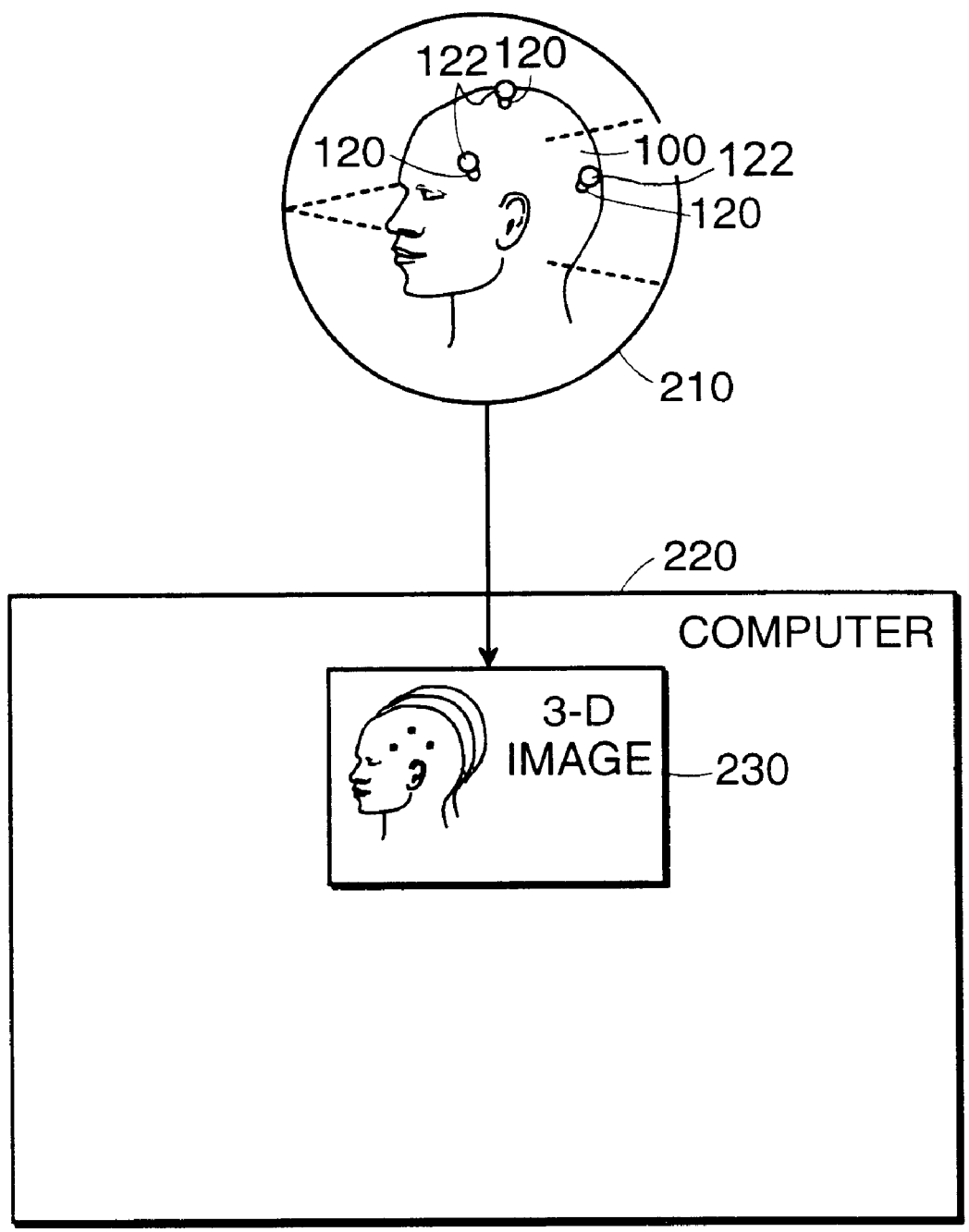
FIG. 2 illustrates a scanning phase.

Referring to FIG. 2, after scanning markers 122 are attached to bone anchors 120, the patient is scanned in a scanner 210 (illustrated schematically) producing a three-dimensional image 230. This image is transferred to a computer 220 where it is stored.

After the scanning process is complete, scanning markers 122 are removed from the patient, but bone anchors 120 are left firmly in place. In a typical situation, because the surgical phase of the process will not begin for several hours, or even several days, the patient is allowed to walk around or even allowed to return home at this point.

Figure 3:
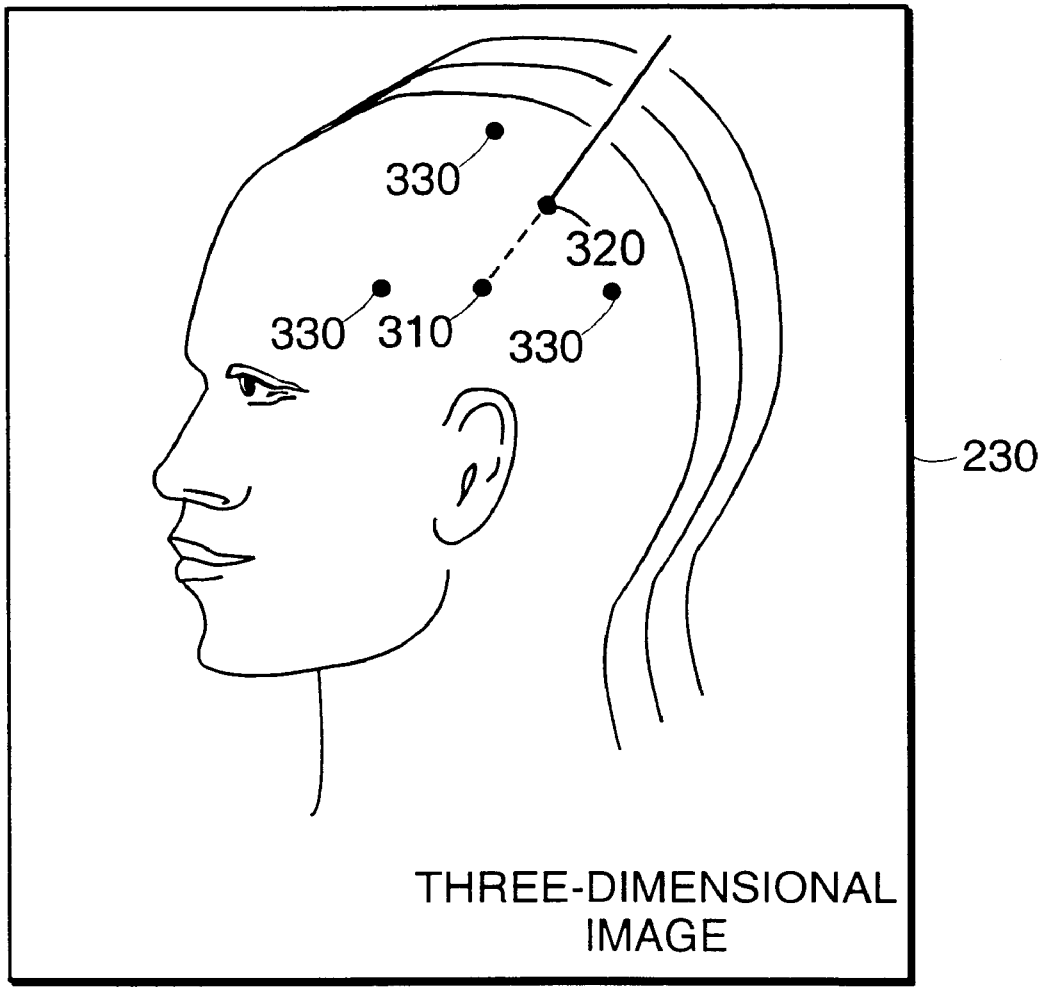
FIG. 3 illustrates a scanned image and located image points.

Referring to FIG. 3, a surgeon plans the upcoming surgery using a computer display of image 230 using well-known techniques in stereotactic surgery. The surgeon identifies a target image point 310 in image 230 corresponding to a target point in the body. The three dimensional coordinates of the target image point in the coordinate system of image 230 are stored on the computer. The surgeon also identifies an entry image point 320 defining a straight-line trajectory by which a surgical instrument can reach the target point while avoiding critical structures in the brain. The coordinates of the entry image point are also stored.

Referring still to FIG. 3, marker image points 330 in image 230 correspond to the marker portions 126 of scanning markers 122 (FIG. 1b). The surgeon can locate these points using the computer display in a similar manner to locating the target and entry points. Alternatively, an automated algorithm is implemented on computer 220 to locate marker image points 330 based on the image characteristics, such as brightness or shape, of the points. In either case, the coordinates in the image of marker image points 330 are stored.

At this point, based on a known correspondence of the scanned image to the physical body, the locations of the actual target and entry points on the body with respect to the locations of the scanning markers are computed and stored on the computer. This computation is based on the stored coordinates of the corresponding marker, target, and entry image points.

A representation of the surface of the skull can be computed directly from the scanned image using well-known image processing techniques. This surface representation can be used to ensure that a designed fixture will properly fit over the skull, or to determine other characteristics of the skull that may be used to design the fixture.

This completes the scanning and surgical planning stage.

Fixture Design Phase

Figure 4:
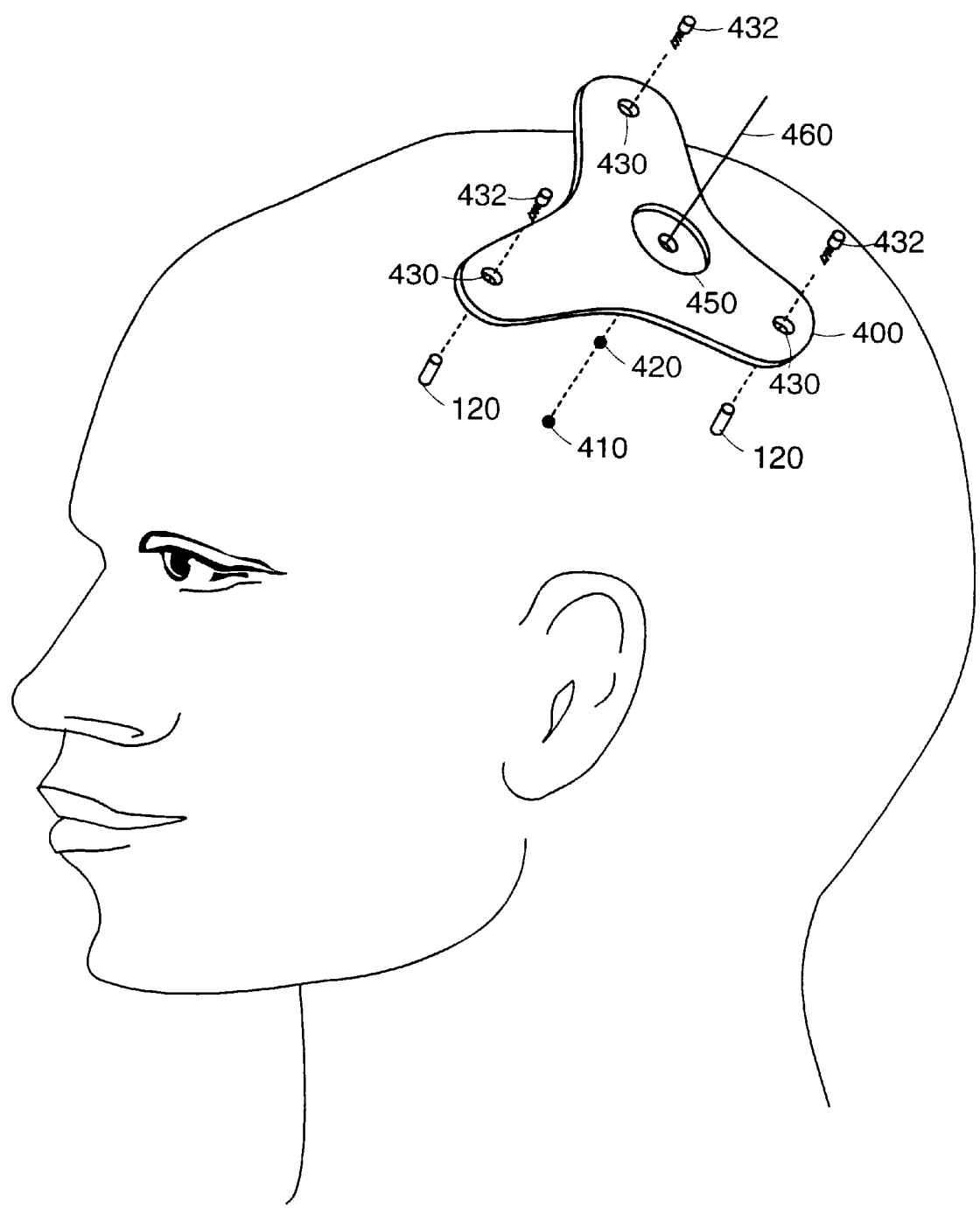
FIG. 4 illustrates a customized fixture.

The next phase of the process involves design and fabrication of the fixture itself. The design requirements of the fixture can be understood by referring to FIG. 4 which shows how a fabricated fixture 400 will be attached to bone anchors 120 in the surgical phase. In this embodiment, fixture 400 is attached to bone anchors 120 using bolts 432 which pass through openings 430 in fixture 400. When attached to the bone anchors, mounting points of fixture 400 are located at the prior locations of the marker portions 126 of scanning markers 122.

A planned actual trajectory 460 passes through an actual entry point 420 to an actual target point 410 corresponding to the planned entry image point 320 and target image point 310 (FIG. 3). Trajectory 460 passes through fixture 400 when attached to the skull. Fixture 400 includes a way of mounting an instrument guide onto it to guide a surgical instrument along trajectory 460. In this embodiment, fixture 400 includes a mounting base 450 for attaching an instrument guide. Mounting base 450 has a flat surface with a central opening. When fixture 400 is attached to the skull, trajectory 460 passes through the central opening of the mounting base and the flat surface of mounting base 450 is perpendicular to trajectory 460. The distance between target point 410 and the mounting base is also determined before the surgical phase, for example by designing the fixture so that this distance is a standard distance related to the type of instrument that will be used.

The design of fixture 400 for a particular patient and surgical procedure must satisfy several constrains including one or more of the following:
1. mounting base 450 is centered on the planned trajectory and oriented perpendicular to the trajectory,
2. the mounting points of fixture 400 mate with bone anchors 120,
3. the distance between target point 410 and the mounting base must be an exact distance or within a particular range related to the surgical instrument and guide that will be used,
4. the orientation of the fixture at each of the mounting points must be appropriate for the orientation of the corresponding bone anchors, and
5. the fixture must provide sufficient clearance above the skull when mounted.

Figure 5A:
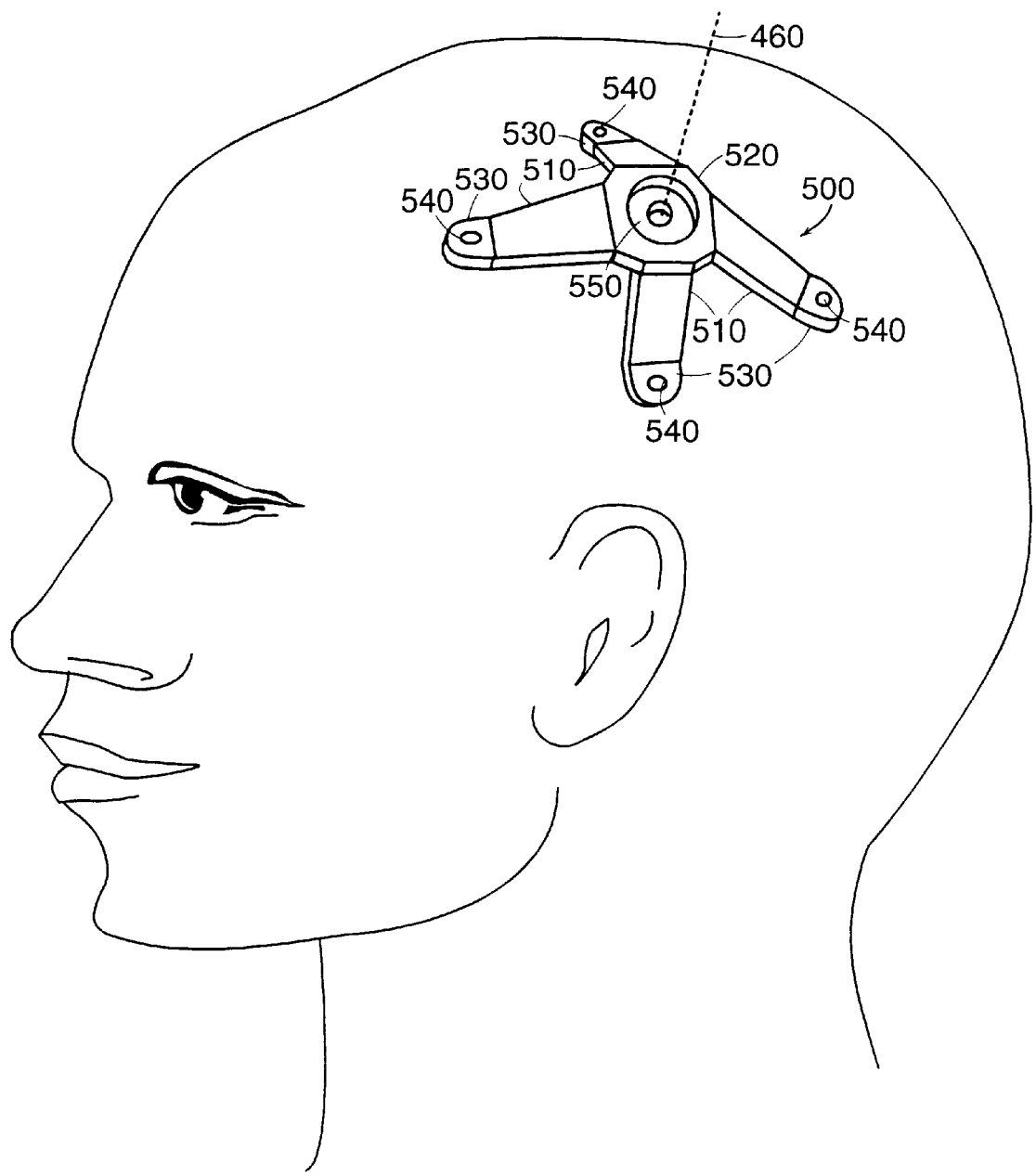
FIGS. 5a–c illustrate another customized fixture, attached to a head, and viewed along a target trajectory and from the side.
Figure 5B:
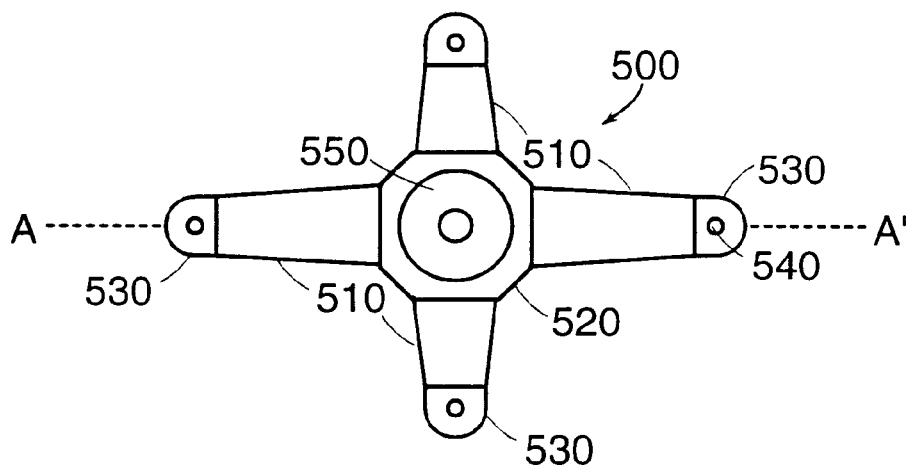
Figure 5C:
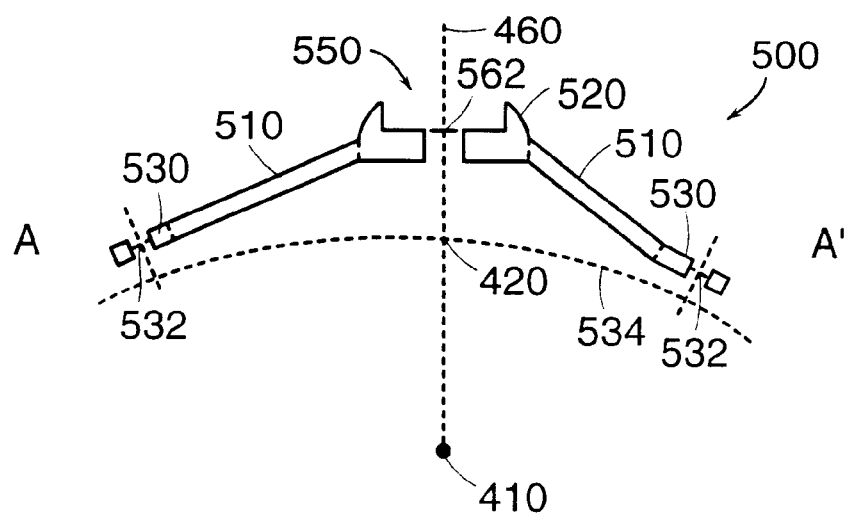

Referring to FIGS. 5a–c, an second exemplary fixture 500 is shown attached to the patient's head (FIG. 5a) and shown in a view along the planned trajectory (FIG. 5b) and in cross section (FIG. 5c). Fixture 500 is designed to attach to four bone anchors. Fixture 500 has a central mounting base 550 in a center section 520. Four "legs" 510 extend from the center section to four mounting pads 530 with mounting holes 540 through which fixture 500 is attached to the bone anchors.

The procedure for satisfying the constraints identified above uses an algorithmic approach. The approach can be understood with reference to FIGS. 5b–c. Referring to FIG. 5c, mounting base 550 is centered on planed trajectory 460. In this example, the distance between target point 410 and the center point 562 of the mounting base is set to a predetermined fixed distance.

Referring still to FIG. 5c, two of the mounting points 532 are illustrated along with the axes of the bone anchors. Mounting pads 530 are designed as planar sections to lie over the mounting points and to be perpendicular to the axes of the bone anchors. Legs 510 are then designed as planar sections that join mounting pads 530 and center section 520.

In FIG. 5c, the surface of the skull 534 is illustrated along with entry point 420. The mounting pads, legs, and center section are design to lie above and provide sufficient clearance above the skull.

In order to orient mounting pads 530 perpendicularly to the axes of the bone anchors, this approach to designing fixture 500 relies on knowledge of the orientations as well as the locations of the bone anchors. In the approach described above, as shown in FIG. 1b, a single marking portion 126 is attached in scanning marker 122 to each bone anchor 120. Therefore only the location of each bone anchor is determined by locating the marker images of the scanning markers.

One of several alternative approaches to determining the orientation of the bone anchors can be used. First, alternative scanning markers 122 can be used. The alternative scanning markers have two marking portions 126 separated along the axis of the scanning marker. Locating the images of both the marking portions determines the orientation of the bone anchor. A second alternative is to use a normal direction to a surface models of the skull. The surface model of the skull can be computed directly from the scanned image using well known image processing techniques. A third alternative is to approximate the orientation of the bone anchors by fitting a surface through the locations of the scanning markers, and optionally through the entry point. A forth alternative is to not rely on the mounting pads being normal to the axes of the bone anchors, relying instead on a mounting approach that is less sensitive to the orientation or the anchors. For instance, a ball can be mounted on each bone anchor and the fixture can have corresponding sockets which mate with the balls.

Fixture 500 shown in FIGS. 5a–c is made up of essentially planar sections. Alternative algorithmic design approaches can be used to design curved structures. For instance, the shape of the fixture can be determined using a surface spline with the mounting points and the mounting base being points at which constraints on the coefficients of the splines are determined.

The design of the customized fixture is converted into a computerized specification of a solid model. A solid model is a computer representation of a volume enclosed by a surface surrounding the entire volume. Various types of computer representations of the volume can be used. A common format is an ".stl" file that is used by many computer aided design (CAD) systems. The .stl file includes a set of representations of surface patches that together define a complete surface that encloses the volume. The .stl file for the designed fixture is then used as the specification for fabrication of the fixture.

Fixture Fabrication

The solid model file is transferred to a rapid prototyping and tooling (RTP) machine. The file can be transferred on a physical medium, such as a magnetic disk, sent over a data network, or used directly on the computer on which is was computed.

A variety of RTP techniques can be used to fabricate the fixture. In this embodiment, a Fused Deposition Modeling (FDM) machine, such model FMD2000 manufactured by Stratasys, Inc. of Eden Prairie Minn., is used to make the three dimensional fixture from the .stl file. The FDM machine essentially robotically lays down a long ribbon of extruded material thereby slowly building up the modeled fixture. As material is laid down, it fuses with the previously laid down material making a homogeneous solid. The process results in a highly accurate fixture, within 5 mil of the specification in the .stl file. Various materials can be used for the fixture. In the embodiment, medical grade ABS is used.

After fabrication in the FDM machine, some further machining may be needed for some fixture designs. For instance, the ABS material can be drilled and tapped to provide mounting points at which an instrument guide is attached.

Surgery

The completed fixture is returned to the surgeon. The patient returns, with the bone anchors still intact, for the surgical phase. The fixture is sterilized and then the surgeon attaches the sterilized fixture to the bone anchors in the patient's skull and begins the surgical phase.

The surgical phase for brain surgery involves several steps, including opening a burr hole, and the inserting of an instrument in the burr hole. The burr hole can be drilled prior to attaching the fixture, or can be drilled using the fixture. In the latter case, a drill guide is attached to the mounting base and a drill is inserted through the drill guide to drill the burr hole at the planned entry point.

Figure 6:
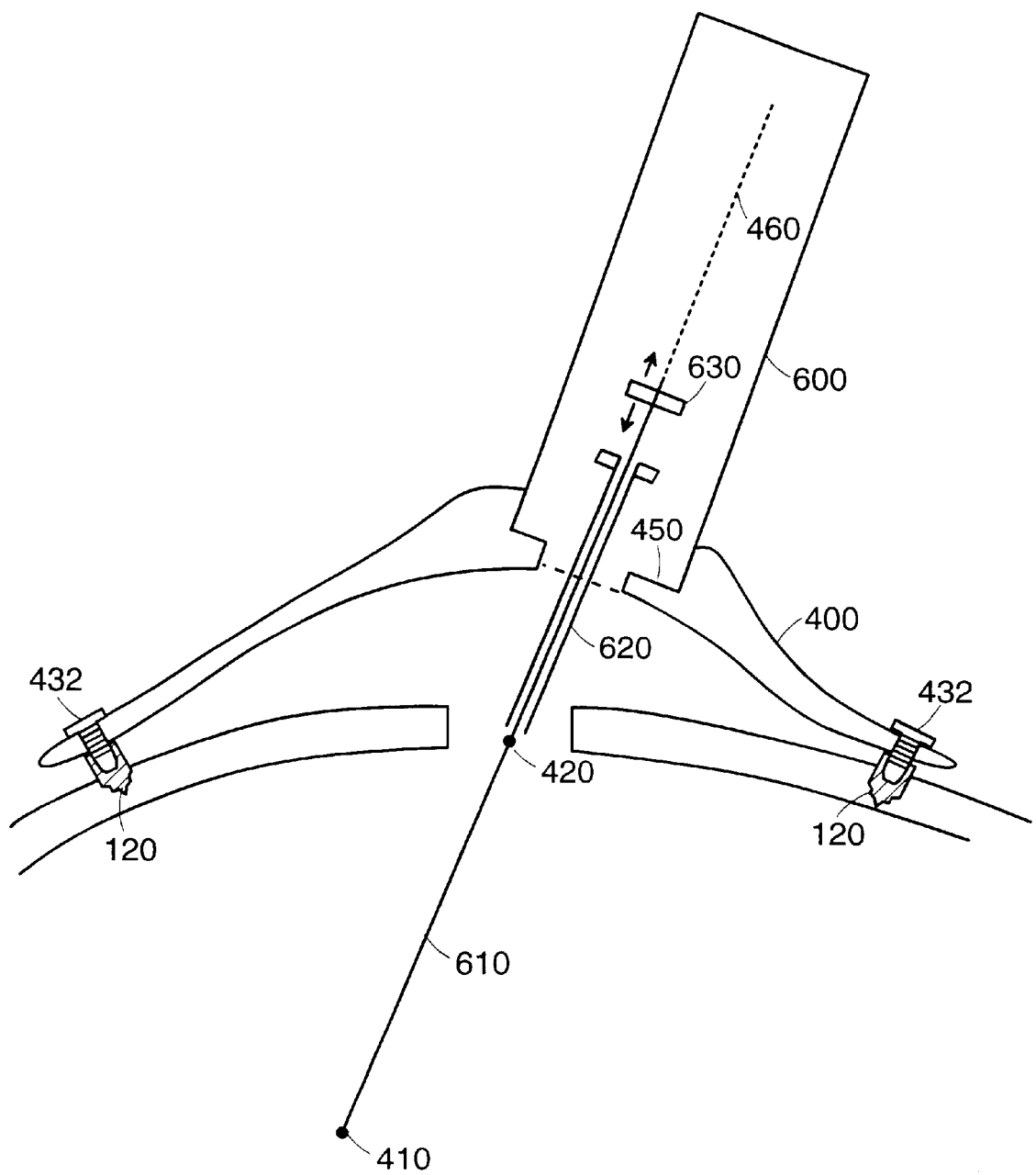
FIG. 6 is a side view of a fixture supporting an instrument guide.

Referring to FIG. 6, to insert a surgical instrument into the brain to reach the planned target point, fixture 400 is used to support an instrument guide 600. In the illustrative example shown in FIG. 6, instrument guide 600 supports an insertion tube 620 through which an instrument 610, such as a recording electrode, is passes. The instrument is attached to a drive 630 on instrument guide 600 for manually or automatically driving the instrument to target point 410. Since the separation of target point 410 and mounting base 450 is specified when the fixture is designed, if the length of the surgical instrument is predetermined, then the instrument guide can be calibrated to precisely insert the instrument to the target point. For instance, if the instrument is known to have a standard length, the separation of the target point and the mounting base on the fixture can be designed such that when the instrument drive is in its fully inserted position, the instrument has reached the planned target point.

Figure 7:
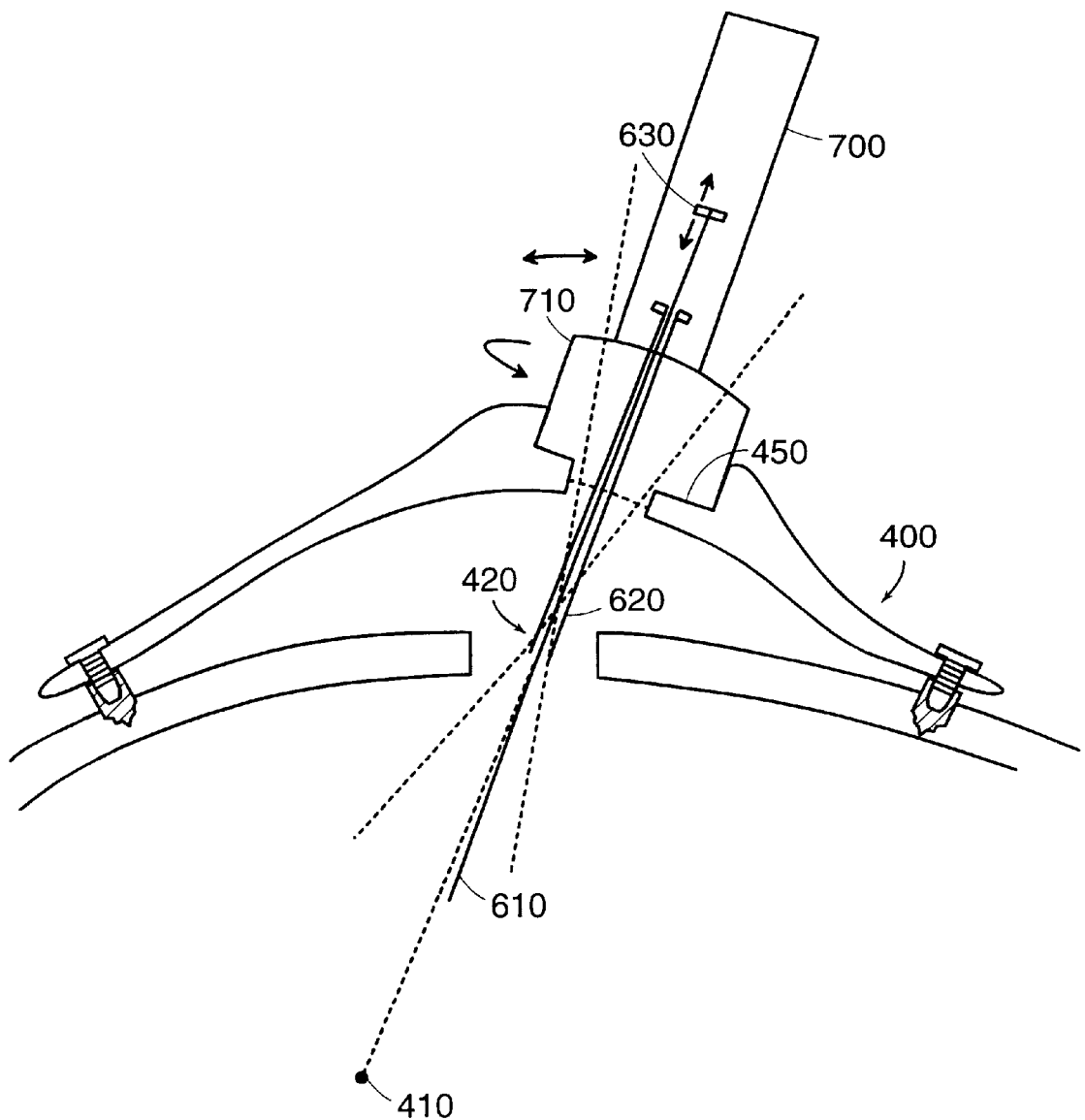
FIG. 7 is a side view of a fixture supporting an adjustable instrument guide.

Alternative instrument guides can be used in conjunction with a custom fabricated fixture. Referring to FIG. 7, an adjustable instrument guide 700 is attached to mounting base 450. The instrument guide is adjustable allowing the actual trajectory of instrument 610 to fall within a cone with an apex at entry point 420. For instance, an adjustable guidance fixture such as one described in copending U.S. patent application Ser. No. 09/063,658 filed Apr 21, 1998 or can be used. Both of these copending applications are incorporated herein by reference.

Note that since adjustable instrument guide 700 is attached in a precise relationship to target point 410 and entry point 420, a "registration" step of the type typically carried out in stereotactic surgery is not needed. Furthermore, instrument guide 700 can include encoders that generate signals which encode the adjustment of the actual trajectory relative to the planned trajectory, allowing precise visual feedback to be computed and displayed to a surgeon. Instrument guide can also be actuated allowing remote or robotic control of the instrument and the guide.

Alternative Approaches

Figure 8:
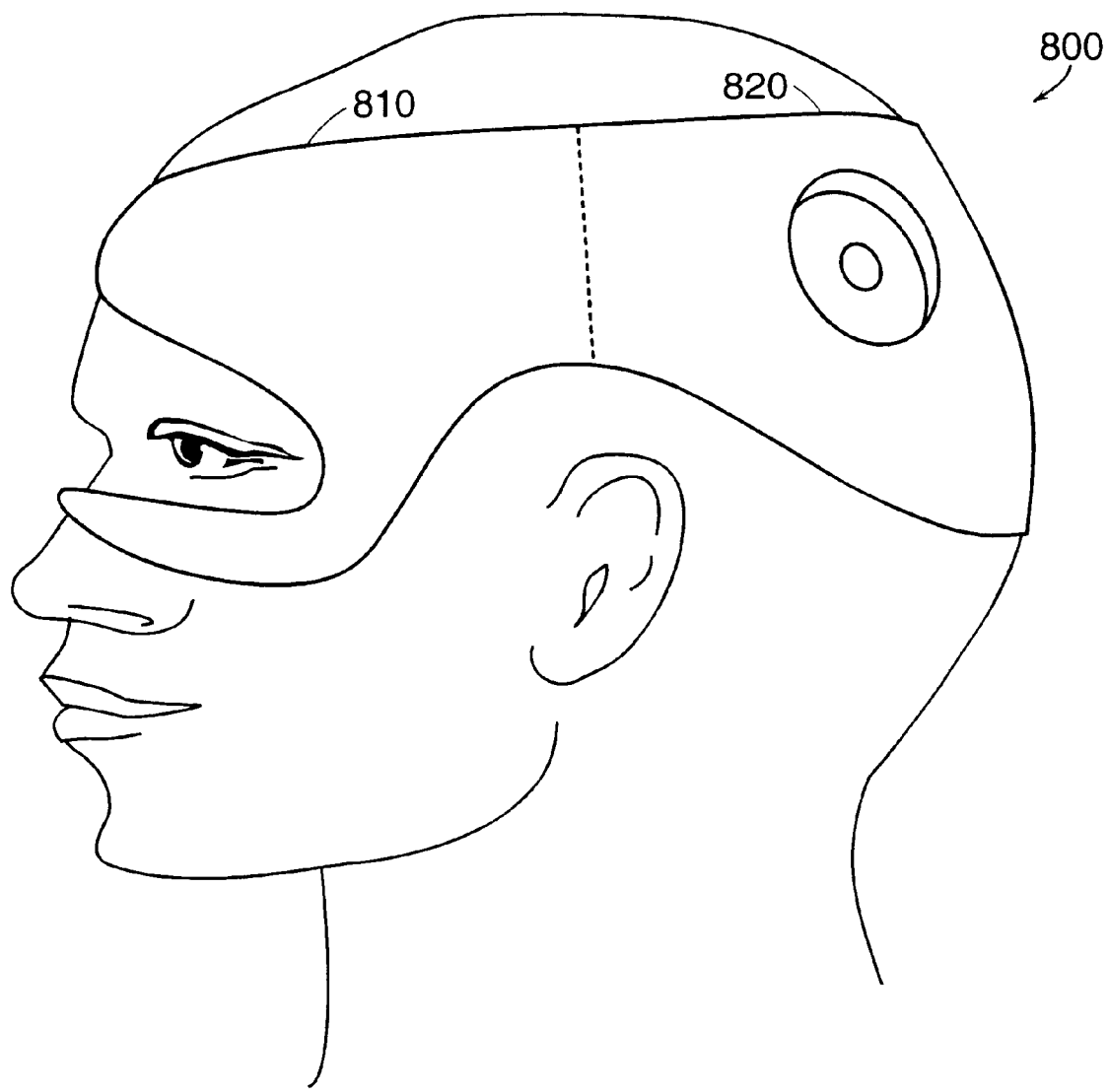
FIG. 8 illustrates a head-mounted fixture which mates with the contours of the skull.

In the embodiment described above, the fabricated fixture is attached to bone anchors. Alternative embodiments attach the fixture to the body in different ways. For instance, other types of inserts or bone anchors can be attached to the skull. Also, rather than attaching the fixture to a bone anchor, the fixture can be designed to precisely clamp onto the patient's head. For example, referring to FIG. 8, two mating halves 810, 820 of a fixture 800 match the contours of cheek bones and forehead, and the contours of the back of the head, respectively. The contours of the patients head are derived from the a model of the skull that is computed automatically from the scanned image.

In the embodiments described above, the design (i.e., the solid model) of the fixture is determined algorithmically from the locations and orientations of points, including the mounting points, the target point and the entry point. An alternative approach to design of the fixture involves interaction with the surgeon. Rather than having to specify a detailed design for the fixture, the surgeon has control over a limited number of deformations of a standard fixture.

A particular implementation of this deformation procedure uses a relational geometry approach. U.S. Pat. No. 5,627,969 issued Mar. 17, 1995 to John S. Letcher, Jr., describes such a relational geometry approach and software architecture to implement the approach.

A set of "standard" fixtures are used as the basis of the procedure. Each of the standard fixtures is described using a "logical model" in which geometric relationships of various elements of the fixture are explicitly identified. Examples of constraints described in the logical model include the shape of the mounting base (which is not deformed), and the connections of sections such as the mounting legs and central section.

In the fixture design phase, the surgeon selects one of the standard fixtures. Using a computer aided graphic design (CAGD) tool, the surgeon views both a representation of the body and a representation of the fixture. Initially, the standard fixture does not satisfy any of the design constraints. Using the CAGD tool, the surgeon adjusts the fixture design so that the fixture will mate with the bone anchor, and so that the mounting base will have the correct location and orientation with respect to the entry and target points. Furthermore, the surgeon can adjust other aspects of the design, for example, deforming the fixture to allow sufficient clearance for an ear.

Spinal Surgery

Another embodiment of the invention is directed to spinal surgery. As in the brain surgery approach, a three-dimensional scanned image is taken of the patient, in this case of his or her spine. No anchor points or scanning markers are necessarily applied to the spine, however.

Figure 9A:
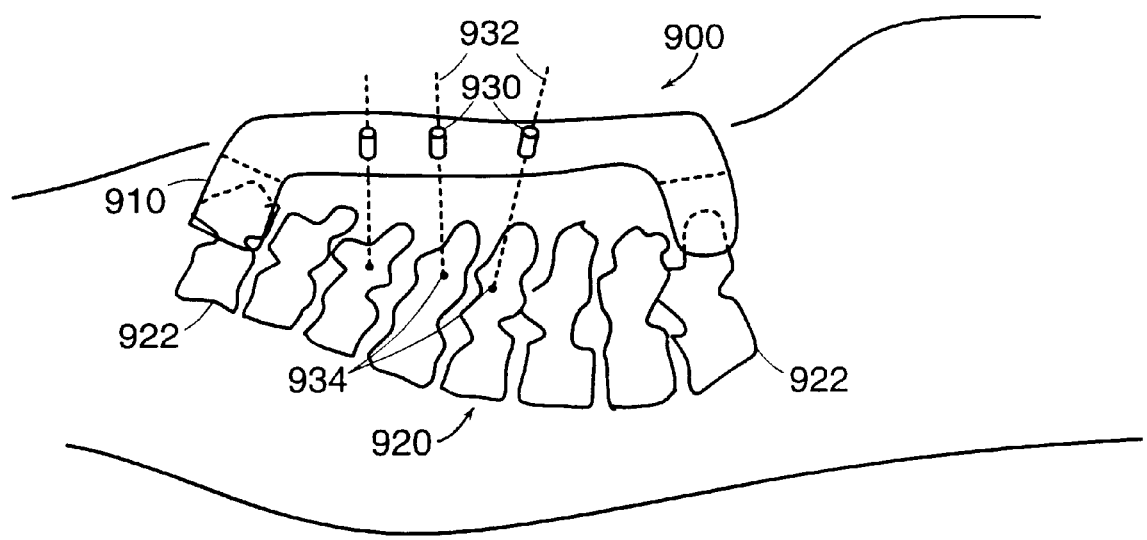
FIGS. 9a–b illustrate a customized fixture for spinal surgery.

Referring to FIG. 9a, using techniques well known in stereotactic spinal surgery, the surgeon identifies target points 934 in the image of a spine 920, for example, points at which screws are to be inserted into the spine. The surgeon also plans trajectories 932 to reach the target points, for example determining the angles at which the screw holes will be drilled.

Using well-known image analysis and modeling techniques, a computer model of the segments of the spine 920 is formed from the scanned image.

Figure 9B:
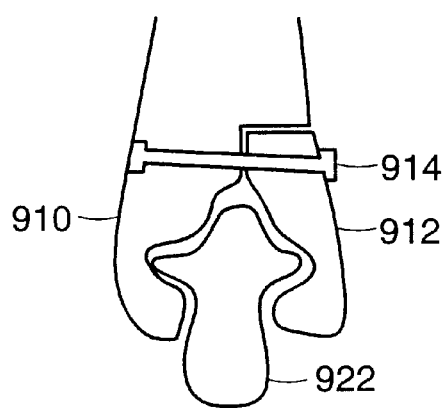

The surgeon identifies two segments 922 to which a customized fixture 900 is to be attached. Referring to FIG. 9b, the models of segments 922 are used to form clamp sections which mate with the contours of the segments. A portion 910 of the clamp section is formed in one piece with the main section of the fixture. A second portion 912 of each clamp section is formed as a separate component. The two portions of the clamp section are drawn together to attach the fixture to the spinal segments. Fixture 900 is formed to match the curvature of spine 920 as it is scanned. For instance, the separation of segments 922 matches the separation in the scanned image.

For each of the target points, a separate instrument guide 930 is formed in fixture 900. For example, each instrument guide can be a elongated hole into which a drill is inserted. The instrument guides can be designed so that not only the orientation but also the depth of the holes drilled into the spinal segments are precisely determined by the instrument guides.

After attaching the fixture, the surgeon proceeds with the operations on each of the spinal segments that are involved in the overall surgery without repositioning fixture 900.

Another embodiment directed to spinal surgery not only addresses operations to be performed on the spine in the configuration that it was scanned, but also address manipulating the spine to a desired curvature different from that in the scanned image. In addition to forming a computer model of the spine as it is scanned, a modified spinal model is also derived. The modified model represents the desired curvature of the spine. A second fixture is designed according to the modified model. After the first fixture is removed, the second fixture is attached to achieve the desired curvature of the spine.

Figure 10A:
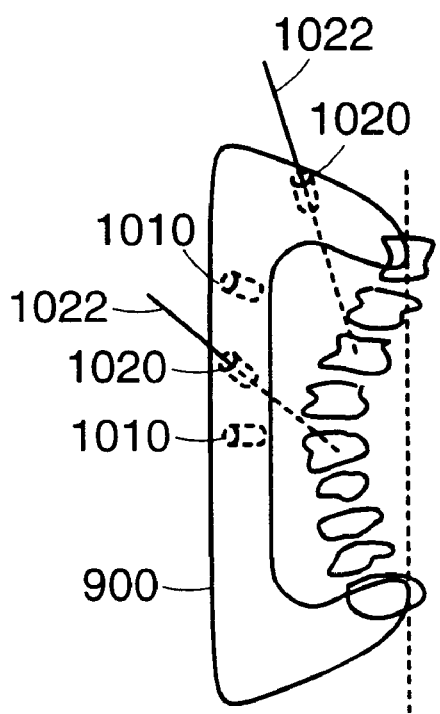
FIGS. 10a–b illustrate a spinal fixture used to modify the curvature of the spine.
Figure 10B:
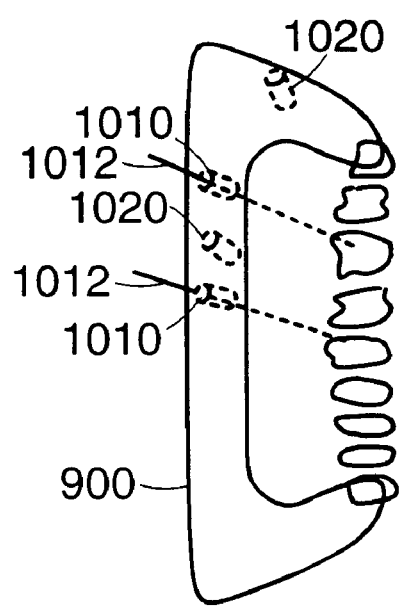

A related embodiment is illustrated schematically in FIGS. 10a–b. This embodiment also uses the modified spinal model. However, rather than forming a second fixture, additional guides 1010 are formed in the first fixture for the purpose of manipulating the spine into the desired configuration. For example, in addition to guides 1020 which are formed along the orientations 1022 to drill the segments, additional guides 1010 are formed in the fixture corresponding to the orientations 1012 of the drilled holes after modification of the curvature, and screws inserted into the holes can be forced to lie in the desired orientations.

Other Surgical Procedures

The embodiments presented above are described in the context of stereotactic brain or spine surgery. Similar approaches are applicable to other types of stereotactic surgery.

Similar customized fixtures are also applicable to other types of surgical procedures in which a device must be precisely attached to a body. For instance, a precise instrument guide can be mounted with reference to facial features for eye surgery.

Implementation

Figure 11:
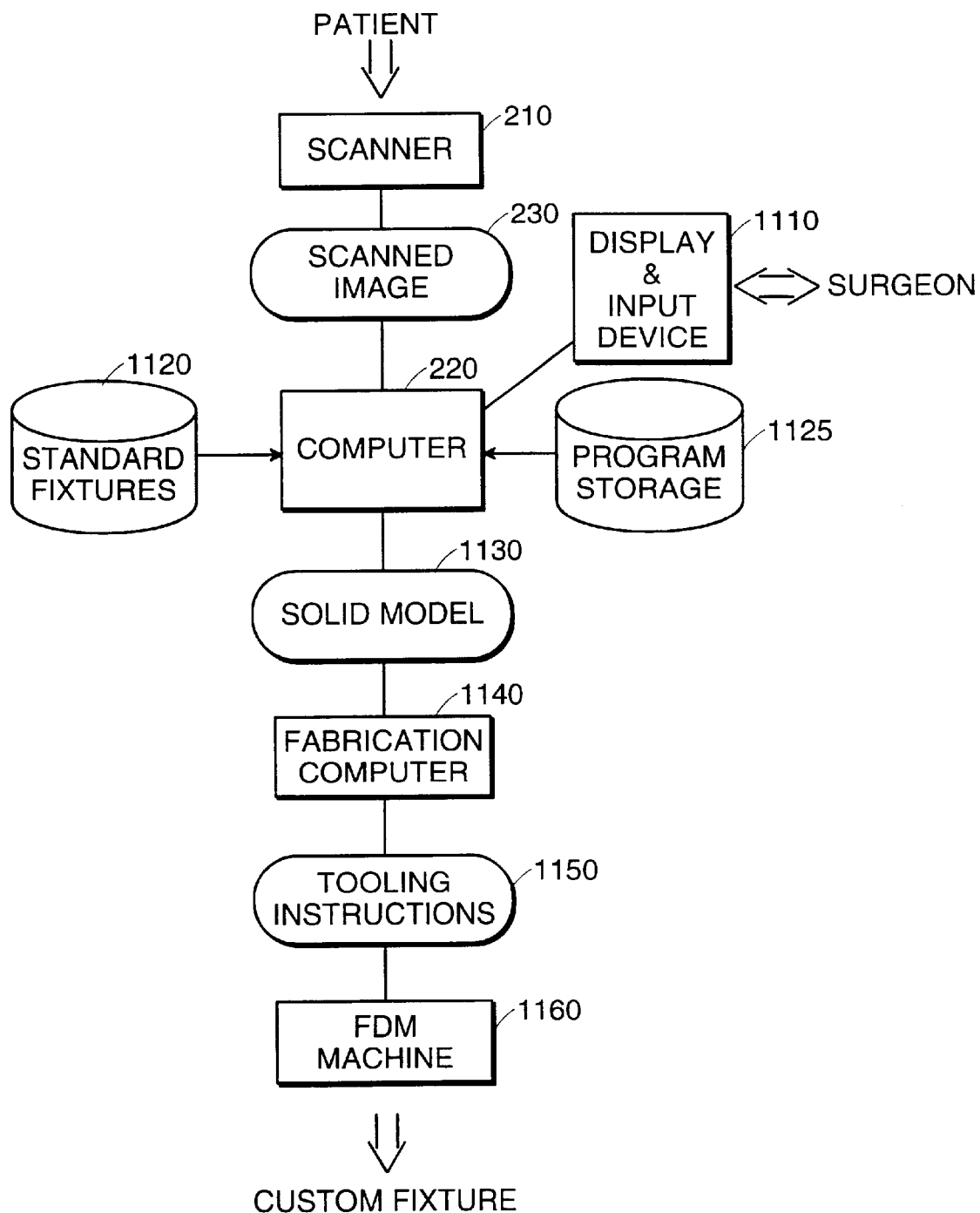
FIG. 11 illustrates a computer implementation of the fixture design procedure.

Referring to FIG. 11, the design and fabrication of the fixture involves several steps and pieces of equipment. Scanner 210 produces scanned image 230 which is passed to computer 220. Computer 220 is used by the surgeon to identify target and entry points, and possibly other points such as marker image points. A display and input device 1110 provides an interface for the surgeon. For instance, multiple planar views of the scanned image are presented to the surgeon, and the surgeon selects points using a mouse. Program storage 1125 is coupled to computer 220 for holding software used to implement procedures executed by computer 220. As described above, a libary of standard fixtures 1120 can optionally be attached to computer 220. These standard fixtures are deformed using interactive procedures implemented on computer 220.

The product of the procedures executed on computer 220 is solid model 1130 which completely specifies the shape of the fixture. This model is passed to a fabrication computer 1140 which derives tooling instructions 1150 which are passed to the FDM machine 1160. The FDM machine fabricates the fixture according to the tooling instructions.

It is to be understood that the foregoing description is intended to illustrate and not limit the scope of the invention, which is defined by the scope of the appended claims. Other embodiments are within the scope of the following claims.

What is claimed is:

1. A method for forming a surgical fixture for attaching to a body and providing a reference structure for precisely locating a target within the body comprising:

processing a three-dimensional scanned image of the body to determine a location of the target within the body relative to a plurality of anchors on the body;

determining data characterizing a structure of the surgical fixture such that when attached to the plurality of anchors the fixture provides a reference structure in a determined location and orientation with respect to the target within the body, wherein the data charactering the structure for the fixture includes a solid model of the fixture which defines the volume enclosed by the surface of the fixture; and fabricating the surgical fixture in accordance with the solid model.

2. The method of claim 1 wherein determining the data characterizing the structure of the surgical fixture includes selecting a model of a standard fixture and deforming the model of the standard fixture in to match the standard model to the target and the mounting location.

3. The method of claim 1 wherein fabricating the surgical fixture includes forming a unitary structure of the fixture using a computer-controlled process.

4. The method of claim 3 wherein forming the unitary structure includes forming said structure using a rapid prototyping and tooling (RPT) technique.

5. A method for using scanning data of a body to design a customized surgical fixture for use during surgery on the body comprising:

accepting the scanning data of the body, wherein said scanning data comprises data characterizing locations of a plurality of anchors on the body relative to a location of a target in the body; and processing the scanning data to compute a digital model of the surgical fixture comprising data that characterizes a shape of said fixture such that said shape includes a plurality of mounting points for attaching the surgical fixture to the anchors on the body;

wherein the shape of the surgical fixture further includes a section for guiding a surgical instrument during surgery on the body such that when said fixture is attached to the anchors, the section for guiding the surgical instrument is in a pre-determined geometric relationship with respect to the target.

6. The method of claim 5 wherein the plurality of anchors include anchors attached to a bone structure in the body and processing the scanning data includes determining coordinates of said anchors.

7. The method of claim 6 wherein the method further includes attaching scanning markers to the anchors prior to scanning the body to produce the scanning data of the body, and wherein determining coordinates of the anchors includes determining coordinates of the scanning markers.

8. The method of claim 6 wherein processing the scanning data further includes determining coordinates of the target and determining a location and an orientation for an instrument guide relative to the mounting points using the coordinates of the target and the coordinates of the anchors.

9. The method of claim 8 wherein determining the location and the orientation for the instrument guide includes determining a trajectory through the body passing through the target, determining the orientation for the instrument guide based on said trajectory and determining the location for the instrument guide based on a distance along said trajectory from the target.

10. The method of claim 8 wherein the section for guiding the surgical instrument includes a mounting base for attaching a removable instrument guide to the surgical fixture.

11. The method of claim 10 wherein mounting base includes a planar region and the section for guiding the surgical instrument includes an opening through the fixture at the mounting base.

12. The method of claim 11 wherein the planar region of the mounting base is in a plane perpendicular to a trajectory from the mounting base to the target when the fixture is attached to the body.

* * * * *